United States Patent [19]

Hall et al.

[11] Patent Number: 4,672,060
[45] Date of Patent: Jun. 9, 1987

[54] ANTIHYPERLIPIDEMIC AMMONIUM POLYBORANES

[75] Inventors: Iris H. Hall, Chapel Hill, N.C.; Robert J. Brotherton, Laguna Beach, Calif.

[73] Assignee: United States Borax & Chemical Corporation, Los Angeles, Calif.

[21] Appl. No.: 788,916

[22] Filed: Oct. 18, 1985

[51] Int. Cl.$^4$ ............................................. A61K 31/69
[52] U.S. Cl. ..................................................... 514/64
[58] Field of Search ............................. 514/64; 546/13

[56] References Cited

U.S. PATENT DOCUMENTS 3,281,218 10/1966 Edwards et al. ...................... 546/13

FOREIGN PATENT DOCUMENTS 776574 1/1968 Canada.
0034238 8/1981 European Pat. Off..

Primary Examiner—Leonard Schenkman
Assistant Examiner—Joseph A. Lipovsky
Attorney, Agent, or Firm—James R. Thornton

[57] ABSTRACT

Ammonium salts of polyboranes are useful as antihyperlipidemic agents for lowering serum cholesterol and triglyceride levels in mammals. Such polyborane ions include the $B_3H_8^-$ and $B_nH_n^=$ groups in which n is 6 to 12.

10 Claims, No Drawings

ANTIHYPERLIPIDEMIC AMMONIUM POLYBORANES

SUMMARY OF THE INVENTION

This invention relates to the use of certain ammonium salts of polyboranes as antihyperlipidemic or hypolipidemic agents to control mammalian diseases associated with increased serum cholesterol or triglyceride levels.

BACKGROUND OF THE INVENTION

Hall et al., J. Pharm. Sci. 70, 339-341 (1981) reported that a series of trimethylamine cyanoboranes and trimethylamine carboxyboranes possess potent hyperlipidemic activity at a dose of 5-20mg/kg/day. These derivatives lowered serum cholesterol levels, reportedly due to the agents' ability to suppress HMG CoA reductase activity. Reduction of serum triglyceride levels was correlated with the inhibition of fatty acid synthetase by the agents. Subsequently, Hall et al., J. Pharm. Sci. 73, 973-977 (1984) reported that tetrakis-u-(trimethylamineborane carboxyato) bis(trimethylaminecarboxyborane)-dicopper (II) was observed to be a potent hypolipidemic agent at the low dose of 2.5 mg/kg in mice. The dicopper complex was observed to lower ATP dependent citrate lyase, acetyl CoA synthetase and phosphatidate phosphohydrolase in vivo and to accelerate cholesterol excretion from the body.

Certain amine borane derivatives which are described as boron analogs of α-amino acids have been patented as antiinflammatory agents. See Spielvogel et al. U.S. Pat. Nos. 4,312,989 and 4,368,194.

Tetramethylammonium hexaborohydride has been disclosed as having herbicidal activity. See Canadian Pat. No. 776,574 issued Jan. 23, 1968 to James L. Boone.

DESCRIPTION OF THE INVENTION

It has been found that the ammonium salts of polyboranes are potent hypolipidemic agents which are effective in decreasing the serum cholesterol and triglyceride levels in mammals.

The polyborane salts of the present invention are the alkylammonium salts of the polyhedral borane ions which can be defined as having the general formula:

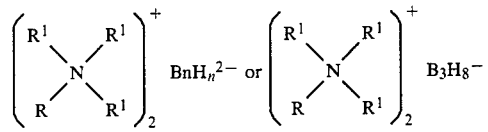

in which R represents alkyl, $R^1$ is alkyl or H and n is an integer of from 6 to 12.

Examples of such polyborane ions include $B_3H_8^-$, $B_6H_6^=$, $B_8H_8^=$, $B_9H_9^=$, $B_{10}H_{10}^=$, $B_{11}H_{11}^=$ and $B_{12}H_{12}^=$. The alkylammonium salts may be the mono-, di-, tri- or tetra-alkylammonium salts, but are preferably the tri- or tetraalkyl-substituted compounds. Lower alkyl groups having from 1 to about 6 carbon atoms are preferred in the ammonium ion.

The polyboranes and their ammonium salts are well known and are readily prepared by known procedures. See, for example, Brotherton and Steinberg, Progress in Boron Chemistry, Volume 2, chapter 1, Permagon Press, 1970; Boone, J. Am. Chem. Soc. 86, 5036 (1964); Miller et al., Inorganic Chemistry 6,1196 (1967); and Muetterties, Boron Hydride Chemistry, Academic Press, 1975, especially chapter 8 by Middaugh.

The ammonium polyboranes of this invention are effective hyperlipidemic agents, being effective both after intraparenteral and oral administration. They have been found to significantly decrease serum cholesterol and serum triglycerides in mice. When the compounds are employed as hypolipidemic agents, they can be administered to warm-blooded mammals such as mice, rats, rabbits, dogs, cats, monkeys, etc. alone or in combination with pharmacologically acceptable carriers, the proportion of which is determined by the solubility and chemical nature of the compounds, the chosen route of administration and standard biological practice. For example, they may be administered orally in the form of tablets, capsules, lozenges, and the like containing extenders such as starch, milk sugar, etc. They may also be administered orally in the form of solutions or they may be injected parenterally. For parenteral administration they may be used in the form of sterile solutions containing other solutes, for example, enough saline or glucose to make the solution isotonic.

The dosage of the compounds will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in the range of from about 4 mg. to about 40 mg. per kilo per day, although as mentioned above, variations will occur.

EXAMPLE

For determining hypolipidemic activity, representative compounds of this invention were suspended in an aqueous 1% 1% carboxymethylcellulose solution and tested at 5 or 20 mg./kg./day administered intraparenterally to male $CF_1$ mice (~25 g.). On days 9 and 16, blood was collected by tail vein bleeding and the serum separated by centrifugation for three minutes. Serum cholesterol levels were determined by a modified Liebermann-Burchard reaction. Serum triglyceride levels were also determined at 16 days using a Fisher-Hycel Triglyceride Test Kit. The results are presented in the following Table.

|  |  | % of Control | | |
|---|---|---|---|---|
|  |  | Serum Cholesterol | | Serum Triglyceride |
| Compound | mg./kg. | Day 9 | Day 16 | Day 16 |
| A | 5 | 92 | 69 | 86 |
| B | 20 | 78 | 73 | 73 |
| C | 20 | 89 | 73 | 55 |
| D | 20 | 82 | 71 | 55 |
| 1% CMC |  | 100 | 100 | 100 |

Cmpd. A = tetramethylammonium triborohydride $(CH_3)_4NB_3H_8$
Cmpd. B = tetramethylammonium hexaborohydride $[(CH_3)_4N]_2B_6H_6$
Cmpd. C = tetramethylammonium dodecaborohydride $[(CH_3)_4N]_2B_{12}H_{12}$
Cmpd. D = triethylammonium dodecaborohydride $[(C_2H_5)_3NH]_2B_{12}H_{12}$ Various changes and modifications of the invention can be made, and to the extent that such variations incorporate the spirit of this invention, they are intended to be included within the scope of the appended claims.

What is claimed is:

1. The method of controlling hyperlipidemia in mammals which comprises administering to said mammal in need thereof an effective amount of an alkylammonium salt of a polyborane of a formula selected from

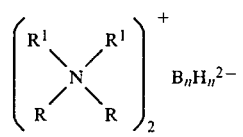

and

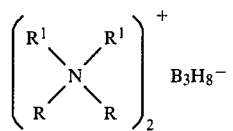

in which R represents lower alkyl, $R^1$ is lower alkyl or H and n is an integer of from 6 to 12.

2. The method according to claim 1 in which said polyborane is a triborohydride.

3. The method according to claim 1 in which said polyborane is a hexaborohydride.

4. The method according to claim 1 in which said polyborane is a dodecaborohydride.

5. The method according to claim 1 in which said alkylammonium ion has at least 3 lower alkyl groups.

6. The method according to claim 1 in which said salt of polyborane is tetramethylammonium hexaborohydride.

7. The method according to claim 1 in which said salt of polyborane is tetramethylammonium dodecaborohydride.

8. The method according to claim 1 in which said salt of polyborane is triethylammonium dodecaborohydride.

9. The method according to claim 1 in which said salt of polyborane is tetramethylammonium triborohydride.

10. The method according to claim 1 in which said polyborane salt is administered at a dosage of from about 4 to about 40 mg./kg./day.